US00PP28944P2

(12) United States Plant Patent
Van Swieten

(10) Patent No.: US PP28,944 P2
(45) Date of Patent: Feb. 6, 2018

(54) ***PHALAENOPSIS* ORCHID PLANT NAMED 'PHALFOREI'**

(50) Latin Name: ***Phalaenopsis* hybrid**
Varietal Denomination: PHALFOREI

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 8 days.

(21) Appl. No.: 14/999,881

(22) Filed: Jul. 13, 2016

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO Plant Variety Database citataion for 'PHALFOREI' Sep. 6, 2017.*
EU Community Plant Variety Rights Application No. 2016/0967, Application n°A201600656, filed Apr. 18, 2016, 8 pages.
EU Community Plant Variety Office Official Gazette, 3.2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFOREI', particularly characterized by having very white flowers, 1 to 3 peduncles that are medium-long and sturdy, leaves that are obovate, and is propagated by meristem tissue culture, is disclosed.

3 Drawing Sheets

Genus and species: *Phalaenopsis* hybrid.
Variety denomination: 'PHALFOREI'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOREI'.

The new *Phalaenopsis* plant is a product of a planned breeding program conducted by the inventor in Bleiswijk, The Netherlands. The objective of this breeding program was to create a new *Phalaenopsis* plant with numerous attractive and unique very white flowers, suitable for potted plant production.

The new *Phalaenopsis* plant 'PHALFOREI' is a result of cross-pollination made by the inventor in March 2007 in Bleiswijk, The Netherlands of the proprietary female, or seed parent, *Phalaenopsis* hybrid '22480-01' (unpatented) with the proprietary male, or pollen parent, Phalaenopsis hybrid '01-1849' (unpatented).

The new *Phalaenopsis* was selected by the inventor as a single plant within the progeny of the stated cross-pollination in a controlled greenhouse in Bleiswijk, The Netherlands in March 2007. Asexual reproduction of the new *Phalaenopsis* plant by meristem tissue culture since 2010 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFOREI' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFOREI' as a new and distinct variety of *Phalaenopsis* plant.

1) Very white flowers;
2) 1 to 3 peduncles;
3) Peduncle is medium-long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in May 2016. Colors in the photographs may differ from the color values cited in the detailed botanical description, which accurately describe the actual colors of the new variety.

DESCRIPTION OF THE NEW VARIETY

Figure 1:
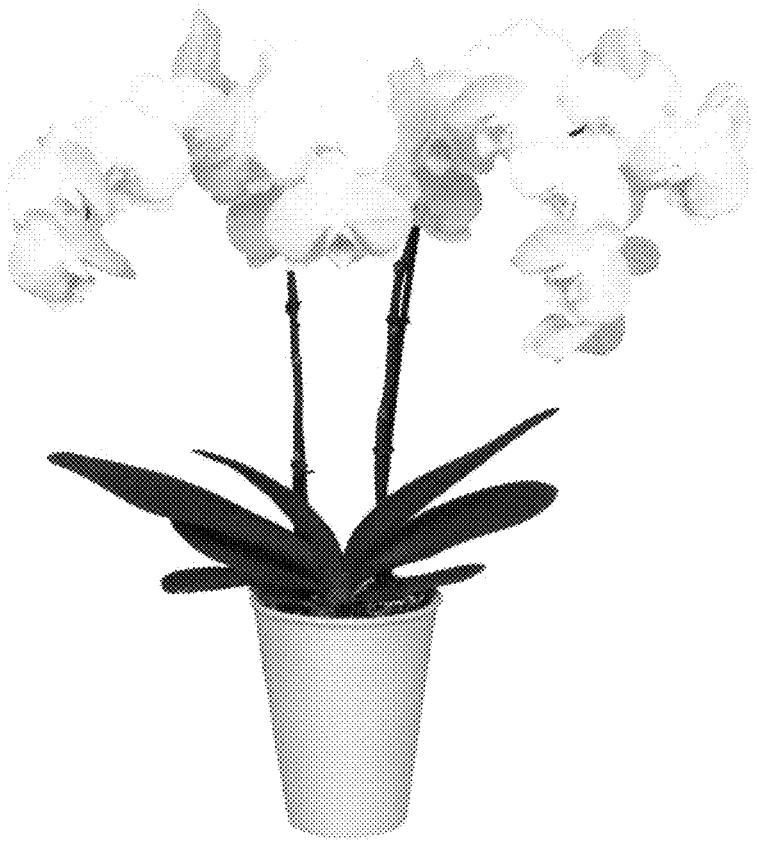
FIG. 1 shows the overall plant habit, including blooms and foliage of 'PHALFOREI'.
Figure 2:
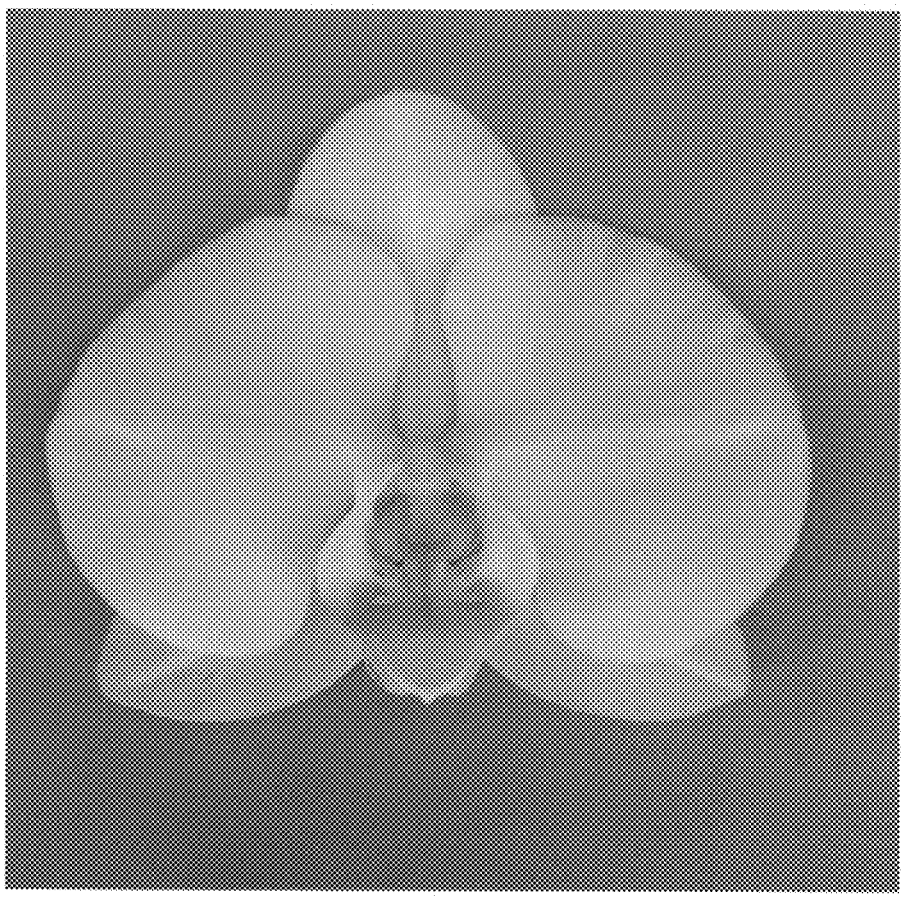
FIG. 2 shows a close-up of a flower of 'PHALFOREI'.
Figure 3:
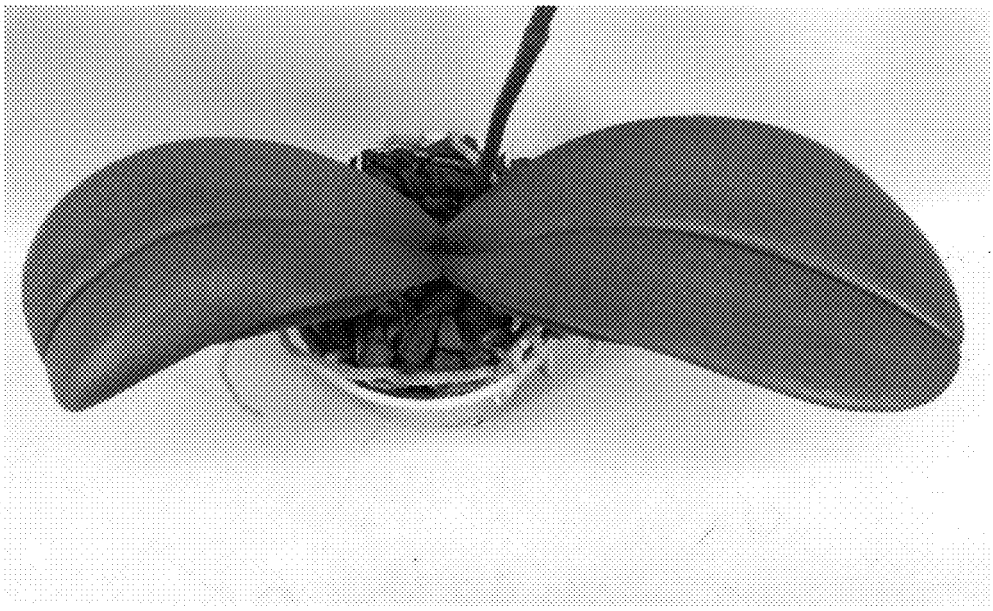
FIG. 3 shows a close-up of the leaves of 'PHALFOREI'.

The following detailed description sets forth the distinctive characteristics of 'PHALFOREI'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALFOREI'.

Parentage:
- *Female parent*.—*Phalaenopsis* cultivar '22480-01' (unpatented).
- *Male parent*.—*Phalaenopsis* cultivar '01-1849' (unpatented).

Propagation:
- *Type*.—Meristem tissue culture.

Roots:
- *Root description*.—Greyed-green colored roots with branching lateral roots having light purple colored root tips.

Plant:
- *Commercial crop time to flowering*.—Approximately 48 to 50 weeks from a rooted cutting to finish in a 12 cm pot.
- *Growth habit of peduncle*.—Standard, green leaves, raceme to panicle.
- *Height* (*from soil level to top of inflorescence*).—Approximately 44.0 cm to 54.0 cm.
- *Width* (*measured from leaf tips*).—About 29.0 cm to 33.0 cm.
- *Vigor*.—Strong.

Leaves:
- *Mature leaves*.—Quantity per plant: 7 to 9 leaves are produced before flowering. Length (fully expanded): 16.0 cm to 19.0 cm. Width: 7.5 cm to 8.5 cm. Shape: Obovate. Base shape: Moderately elongated. Apex: Unequal obtuse. Leaf blade angle with the petiole (measured from the horizontal position): Between 30 degrees and 40 degrees. Leaf margin: Entire. Color: Upper surface: RHS 146A with a touch of diluted RHS 187B. Lower surface: RHS 187B and 146B. Texture: Slightly rough. Thickness: 2.0 mm to 2.3 mm. Venation: Pattern: Parallel. Color of the midvein: Upper surface: RHS N199A. Lower surface: RHS 187B.

Peduncle:
- *Quantity per plant*.—1 to 3.
- *Number of flowers per peduncle*.—11 to 14.
- *Length*.—44.0 cm to 54.0 cm.
- *Diameter*.—5.3 mm to 5.8 mm.
- *Strength*.—Strong.
- *Aspect*.—Upright to slightly pendant.
- *Texture*.—Smooth.
- *Color*.—Mix of brown (RHS N200A) and green (RHS 146C).
- *Internode length*.—4.0 cm to 5.0 cm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base of first flower to tip of inflorescence): 250.0 mm to 280.0 mm.
- *Flowering time*.—First flowers can be expected 10 to 11 months after planting in a 12 cm (diameter) pot.
- *Flower*.—Height: 78.0 mm to 83.0 mm. Diameter: 92.0 mm to 97.0 mm. Depth of lip: 21.0 mm to 23.0 mm.
- *Flower longevity*.—On the plant: 13 to 17 weeks.
- *Fragrance*.—Absent.
- *Flower bud*.—Average size: Medium to large. Length: 22.0 mm to 24.0 mm. Width: 15.0 mm to 17.0 mm. Shape: Egg shaped. Color: Light green (RHS 145C).
- *Petals*.—Arrangement: Open to almost touching. Shape: Semi-circular. Apex: Rounded slightly asymmetric. Margin: Entire. Length (from base to tip): 42.0 mm to 44.0 mm. Width: 56.0 mm to 58.0 mm. Color (when fully opened): Upper surface: Basic color: White (RHS NN155C). Over color: Absent. Lower surface: Basic color: White (RHS NN155C). Over color: Absent.
- *Dorsal sepal*.—Shape: Elliptic broad. Apex: Obtuse symmetric. Margin: Entire. Length (from base to tip): 42.0 mm to 44.0 mm. Width: 32.0 mm to 34.0 mm. Color (when fully opened): Upper surface: Basic color: White (RHS NN155C). Over color: Absent. Lower surface: Basic color: White (RHS NN155C). Over color: Absent.
- *Lateral sepals*.—Shape: Ovate. Apex: Obtuse asymmetric. Margin: Entire. Length (from base to tip): 46.0 mm to 48.0 mm. Width: 26.0 mm to 28.0 mm. Color (when fully opened): Upper surface: Basic color: White (RHS NN155C). Over color: Light green at the base (RHS 145B). Lower surface: Basic color: White (RHS NN155C). Over color: Light green at the base (RHS 145B).
- *Labellum* (*lip*).—Margin: Entire. Whiskers: Present. Length of whiskers: 19.0 mm to 21.0 mm. Color of whiskers: Yellow (RHS 6C). Pubescence on the lip: Absent.
- *Lateral lobe*.—Shape: Spatulate. Length (from base to tip): 21.0 mm to 23.0 mm. Width: 19.0 mm to 21.0 mm. Color: White (RHS NN155C) with yellow-green on one side (RHS 154B) and a few stripes at the base (RHS 174A).
- *Apical lobe*.—Shape: Triangular. Length: 23.0 mm to 25.0 mm. Width: 22.0 mm to 24.0 mm. Color: White (RHS NN155C) and yellow-green towards the callus (RHS 154B).

*Callus*.—Average size: Medium. Height: 0.6 cm to 0.7 cm. Length: 0.5 cm to 0.6 cm. Width: 0.5 cm to 0.6 cm. Color: Yellow (RHS 7C/D) with small dots (RHS 174B).

*Reproductive organs*.—Column: Length: 8.0 mm to 10.0 mm. Diameter: 5.6 mm to 5.8 mm. Color: White (RHS NN155C). Pollinia: Quantity: 2. Diameter: 1.2 mm to 1.4 mm. Color: Yellow-orange (RHS 23A). Ovary: Length: 7.0 mm to 9.0 mm. Diameter: 2.3 mm to 2.5 mm. Pedicel: Length: 39.0 mm to 41.0 mm. Diameter: 2.8 mm to 3.0 mm. Color: Light green (RHS 145C).

Disease, pest, and stress resistance: No specific resistance or susceptibility observed to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

'PHALFOREI' differs from the female parent plant '22480-01' (unpatented), in that 'PHALFOREI' has wider flowers and taller plants than '22480-01'.

'PHALFOREI' differs from the male parent plant '01-1849' (unpatented), in that 'PHALFOREI' has more narrow flowers, shorter whiskers and shorter plants than '01-1849'.

'PHALFOREI' is most similar to the commercial *Phalaenopsis* varieties 'PHALCARDOK' (U.S. Plant Pat. No. 25,447) and 'PHALDIPWEQ' (U.S. Plant Pat. No. 26,466). 'PHALFOREI' differs from the commercial variety 'PHALCARDOK' in that 'PHALFOREI' has lateral sepals with a light green (RHS 145B) lower surface overcolor, callus that are yellow (RHS 7C/D), and no overcolor of the dorsal sepal lower surface, whereas 'PHALCARDOK' has lateral sepals with a light green (RHS 144D) lower surface overcolor, callus that are orange (RHS 168C), and a light purple (RHS 77D) overcolor of the dorsal sepal lower surface. Additionally, 'PHALFOREI' has more narrow flowers, shorter leaves and shorter whiskers than 'PHALCARDOK'.

'PHALFOREI' differs from the commercial variety 'PHALDIPWEQ' in that 'PHALFOREI' has lateral sepals with a light green (RHS 145B) lower surface overcolor, callus that are yellow (RHS 7C/D), and no overcolor of the dorsal sepal lower surface, whereas 'PHALDIPWEQ' has lateral sepals with a light purple (RHS 77D) lower surface overcolor, callus that are yellow orange (RHS 17B), and a light purple (RHS 77D) overcolor of the dorsal sepal lower surface. Additionally, 'PHALFOREI' has more narrow flowers, shorter leaves and shorter whiskers than 'PHALDIPWEQ'.

I claim:

1. A new and distinct variety of *Phalaenopsis* plant named 'PHALFOREI', substantially as described and illustrated herein.

* * * * *